United States Patent [19]

Ferrari

[11] Patent Number: 5,227,162
[45] Date of Patent: Jul. 13, 1993

[54] ACARICIDAL COMPOSITION AND USE THEREOF IN DISINFESTING TREATMENTS

[75] Inventor: Carlo Ferrari, Moncalieri, Italy
[73] Assignee: Officine Ferrari s.n.c. di Carlo e Mario Ferrari & Co., Turin, Italy
[21] Appl. No.: 635,102
[22] PCT Filed: May 9, 1990
[86] PCT No.: PCT/EP90/00744
  § 371 Date: Jan. 7, 1991
  § 102(e) Date: Jan. 7, 1991
[87] PCT Pub. No.: WO90/14012
  PCT Pub. Date: Nov. 29, 1990
[51] Int. Cl.⁵ .................... A61K 35/78; A61K 33/04
[52] U.S. Cl. ................... 424/195.1; 424/703; 424/DIG. 10; 514/919
[58] Field of Search ............ 424/195.1, DIG. 10, 424/703; 514/919

[56] References Cited
FOREIGN PATENT DOCUMENTS 1767616 12/1971 Fed. Rep. of Germany .
2565782 12/1985 France .
193276  5/1938 Switzerland .

OTHER PUBLICATIONS

King, Chemicals Evaluated as Insecticides and Repellants at Orlando Fla. USDA, Handbook No. 69, 1954, p. 321.
Chem. Abst. Smith et al., 82:94140p, 1975.
Chem. Abst. Gubler et al 49:9860f, 1954.
Chem. Abst. Catár 49:2002f 1954.

Primary Examiner—John W. Rollins
Attorney, Agent, or Firm—Ratner & Prestia

[57] ABSTRACT

The invention relates to a composition that is effective in fighting infestations from mites, particularly against the *Varroa Jacobsoni acarus*, a honeybees parasite. The composition is constituted by a mixture of elementary sulphur powder, garlic bulbs that have been crushed or reduced to a pulp, ethanol, and in case, dried pepper powder. In a preferred composition the above components are present in weight ratios of 30:30:30:10, respectively. The invention further includes the use of the composition as an acaricidal agent in treatments of disinfestation, as well as the preventive use thereof for prophylaxis purposes.

6 Claims, No Drawings

ACARICIDAL COMPOSITION AND USE THEREOF IN DISINFESTING TREATMENTS

The present invention relates to an acaricidal composition, particularly to a composition that is effective against the *Varroa Jacobsoni acarus*.

The invention further refers to the use of such a composition in the struggle against mites, both as a pesticidal agent and for prophylaxis purpose.

It is known that the *Varroa Jacobsoni acarus*, commonly called "varroa", is a vermin of the bees—particularly the *Apis mellifica* bee—that infests the hives causing heavy economical losses, settling as a preference in the male cells.

The treatments employed to fight the infestation of varroa are either mechanical or chemical.

Mechanical treatments consist in providing the beehives with traps exploiting the mite's preference for the male cells. However positive results are achieved slowly and are not very satisfying since the traps only limit the infestation.

The chemical treatments consist in applying synthetic pesticides. Under these conditions, there exists a toxicity problem for the beekeeper employing the pesticide, as well as a contamination problem of the produced honey, so that sanitary regulations forbid the treatment with such pesticides near the fertility time of the bees and for a certain time thereafter. Therefore the treatment with synthetic pesticides, although employed by many beekeepers, cannot be considered an effective solution in all respects.

It has now been found a composition that is effective against the *Varroa Jacobsoni acarus* and against many other kinds of mites, that is not a chemical product obtained by synthesis and therefore does not imply the above mentioned drawbacks of the known products. On the contrary, the composition according to the invention is a mixture of natural products that are well tolerated by the bees, as well as by the other animal or vegetable organisms that are infested by mites, and do not contaminate the honey.

Such acaricidal composition according to the invention is generally made up by a mixture of elementary sulphur, crushed garlic bulbs and ethanol.

Garlic bulbs are obtained by the plant of the genus Allium, more particularly of the species Allium sativum. The bulblets are crushed, milled or more preferably reduced to a pulp to form a mush from which, through the use of ethanol, an alcoholic extract is obtained which contains the garlic active ingredients.

Elementary sulphur is used as a fine powder, preferably in the form known as "wettable ventilated sulphur".

Ethanol is both an active ingredient of the composition and the medium for the solution and the suspension of the other components thereof.

The composition according to the invention contains from 20 to 40% by weight of elementary sulphur, from 15 to 35by weight of garlic bulbs, the balance being ethanol.

Depending upon the ethanol amount, the composition appears as a liquid or thick composition which is obtained by mixing the solid components in the liquid medium.

According to another characteristic of the invention, the composition contains also pepper, preferably of the species Capsicum annuum, of sour and piquant varieties, dried and reduced to powder. The amount of dried pepper in the mixture can be between 1 and 15% by weight of the total.

In the preferred embodiment including four components, the composition according to the invention contains from 20 to 40% of elementary sulphur, from 15 to 35% of crushed garlic bulbs, from 1 to 15% of pepper powder, and from 64 to 10% of ethanol, all the components being expressed by weight. The preferred composition contains 30% of elementary sulphur, 30% of garlic bulbs that have been crushed or reduced to a pulp, 30% of 99% by volume ethanol, and 10% of pepper powder, all the components being given by weight.

The composition is prepared by mixing the components in a vessel by means of a mechanical stirrer until it is obtained a sufficiently homogeneous dispersion of the solid parts into the liquid or a paste with a consistency that depends upon the ethanol amount.

Then the composition is applied to the parts that have been infested by the mites, usually by smearing it with a brush.

If the product density so allows, it is possible also a spray application by means of devices that are commonly used for such purposes.

When used against verroa, the composition is smeared over the side walls, bottom walls and over the cover of each hive, and if necessary the application is repeated until the substantial regress or the disappearance of the infestation.

The exact reasons why the composition is so effective as an acaricide agent have not yet been fully investigated and understood. It is supposed that each component carries out a germicidal and antiseptic action resulting in an overall effect that is as deadly to the mites as harmless to the infested organism, be it the bee or another animal or vegetable organism. The composition according to the invention has been particularly developed against the *Varroa Jacobsoni acarus*, since this latter causes quite damaging infestations in apiculture. Nevertheless the composition has been experimented also against other parisitic infestations, such as those affecting chickens or rosebushes, in both cases with positive effects.

Therefore the invention also includes the use of the composition as an acaricide agent, particularly against *Varroa Jacobsoni acarus*.

A few examples illustrating the invention are given hereinbelow.

EXAMPLE 1

In a 250 ml vessel 40 g of double ventilated elementary sulphur and 45 g of 95% by volume ethanol are mixed. 15 g of garlic bulbs are added, in form of bulblets that were deprived of the envelopping membrane, reduced to a pulp in a hydraulic squeezer of stainless steel, aluminum or plastics. Both the juice and the crushed fibrous portion of the garlic are added to the mixture of sulphur and ethanol. The mixture is then stirred by a mechanical stirrer until a homogeneous suspension is obtained.

The composition is applied by means of a brush over the area infested by the mites. After a few weeks a substantial regress of the infestation was reported.

EXAMPLE 2

In a 250 ml vessel 20 g of double ventilated elementary sulphur, 35 g of garlic bulbs as obtained in example 1, and 45 g of 95% by volume ethanol are mixed. The mixture is stirred. This way it is obtained a suspension suitable to be applied by brushing or spraying over the area infested by the mites. After a few weeks a substantial regress of the infestation was reported.

EXAMPLE 3

In a 250 ml vessel 20 g of double ventilated elementary sulphur, 30 g of garlic bulbs as obtained in example 1, 45 g of 99% by volume ethanol and 5 g of dried pepper powder (*Capsicum annuum*) piquant variety are mixed. The mixture is stirred and the resulting suspension is applied by means of a brush over the side walls, the bottom wall and the cover of a hive for breeding Apis mellifica. After three months the hive was inspected and a substantial regress of the infestation was reported.

EXAMPLE 4

In a 250 ml vessel 30 g of double ventilated elementary sulphur, 30 g of crushed garlic bulbs as obtained in example 1, 10 g of dried pepper powder (*Capsicum annuum*) piquant variety, and 30 g of 99% by volume ethanol are mixed. The mixture is stirred by means of a mechanical stirrer to a thick consistency.

The composition is applied to a hive for breeding Apis mellifica infested by Varroa Jacobsoni, located in nortwest Italy, by covering both the side walls and the bottom and the cover of the hive. The application was made in the month of June. The hive bottom was 30×30 cm. After about three months (at the end of August) the hive was inspected and a number of dead mites between 40,000 and 42,000 was counted on the hive bottom. The hive bottom has been cleaned and the treatment has been repeated using the same composition in the same way as above. After about two months (at the end of October) the hive has been inspected again. About 500 dead mites were counted on the hive bottom. After properly cleaning, the treatment has been applied again with the same composition. After about four months (at the end of February in the following year) the inspection was repeated and a single dead mite was found on the hive bottom. An examination of the bees showed the absence of the parasite.

The treatment neither influenced the breeding conditions, nor the quality of the produced honey.

The composition can also be used with prophylaxis purposes against the mites, i.e. as a preventive treatment to avoid the infestation.

I claim:

1. An acaricidal composition comprising 20 to 40% by weight of sulphur powder, 15 to 35% by weight of garlic that has been ground or reduced to a pulp, and 10 to 64% by weight of ethanol.

2. A composition as recited in claim 1, further comprising from 1 to 15% by weight of Capsicum-specific pepper powder.

3. A method of treating an area subject to mite infestation comprising applying to said area a composition comprising 20 to 40% by weight of sulphur powder, 15 to 35% by weight of ground garlic, and 10 to 65% by weight of ethanol.

4. The method of claim 3, wherein said composition further comprises from 1 to 15% by weight of Capsicum-specific pepper powder.

5. A method of treating a bee hive subject to mite infestation comprising applying to the walls of said bee hive a composition comprising 2 to 40% by weight of sulphur powder, 15 to 35% by weight of ground garlic, and 10 to 65% by weight of ethanol.

6. A method of treating a bee hive subject to *Varroa Jacobsoni acarus* infestation comprising applying to the walls of said bee hive a composition comprising 20 to 40% by weight of sulphur powder, 15 to 35% by weight of ground garlic, 10 to 65%.by weight of ethanol, and 1 to 15% by weight of Capsicum-specific pepper powder.

* * * * *